United States Patent
DiBiase et al.

(10) Patent No.: US 8,512,691 B2
(45) Date of Patent: *Aug. 20, 2013

(54) STABLE LIQUID INTERFERON-BETA FORMULATIONS

(75) Inventors: Mary D. DiBiase, Wellesley, MA (US); Wen-Li Chung, Arlington, MA (US); Mark Staples, Cambridge, MA (US); Eric Scharin, Cary, NC (US)

(73) Assignee: Biogen Idec Ma Inc., Weston, MA (US)

( * ) Notice: Subject to any disclaimer, the term of this patent is extended or adjusted under 35 U.S.C. 154(b) by 8 days.

This patent is subject to a terminal disclaimer.

(21) Appl. No.: 11/975,379

(22) Filed: Oct. 18, 2007

(65) Prior Publication Data

US 2008/0050338 A1 Feb. 28, 2008

Related U.S. Application Data

(63) Continuation of application No. 10/397,108, filed on Mar. 24, 2003, now abandoned, which is a continuation of application No. 09/403,930, filed as application No. PCT/US97/23817 on Dec. 23, 1997, now abandoned.

(60) Provisional application No. 60/034,353, filed on Dec. 24, 1996.

(51) Int. Cl.
*A61K 38/21* (2006.01)
*A61K 38/00* (2006.01)
*C07K 14/565* (2006.01)

(52) U.S. Cl.
USPC .................. 424/85.6; 530/351; 514/1.1

(58) Field of Classification Search
None
See application file for complete search history.

(56) References Cited

U.S. PATENT DOCUMENTS

| | | | |
|---|---|---|---|
| 4,252,791 A | 2/1981 | Grossberg et al. | |
| 4,462,940 A | 7/1984 | Hanisch et al. | |
| 4,465,622 A | 8/1984 | Nobuhara et al. | |
| 4,496,537 A | 1/1985 | Kwan | |
| 4,526,782 A | 7/1985 | Uemura et al. | |
| 4,588,585 A | 5/1986 | Mark et al. | |
| 4,605,556 A | 8/1986 | Sato et al. | |
| 4,606,917 A | 8/1986 | Eppstein | |
| 4,647,454 A | 3/1987 | Cymbalista | |
| 4,659,570 A | 4/1987 | Terano | |
| 4,675,183 A | 6/1987 | Kato et al. | |
| 4,675,184 A | 6/1987 | Hasegawa et al. | |
| 4,732,683 A | 3/1988 | Georgiades et al. | |
| 4,822,605 A | 4/1989 | Powell | |
| 4,845,032 A | 7/1989 | Obermeier | |
| 4,847,079 A | 7/1989 | Kwan | |
| 4,857,316 A | 8/1989 | Eppstein | |
| 4,895,716 A * | 1/1990 | Goldstein et al. | 424/85.5 |
| 4,929,442 A | 5/1990 | Powell | |
| 4,957,734 A | 9/1990 | Miller | |
| 4,966,963 A | 10/1990 | Patroni | |
| 4,992,271 A | 2/1991 | Fernandes et al. | |
| 4,992,419 A | 2/1991 | Woog et al. | |
| 4,992,531 A | 2/1991 | Patroni et al. | |
| 5,004,605 A | 4/1991 | Hershenson et al. | |
| 5,008,377 A | 4/1991 | Patroni et al. | |
| 5,124,315 A | 6/1992 | Ceschel et al. | |
| 5,165,921 A | 11/1992 | Ganesh et al. | |
| 5,183,746 A * | 2/1993 | Shaked et al. | 435/69.51 |
| 5,236,707 A | 8/1993 | Stewart, II | |
| 5,270,037 A | 12/1993 | Bienzle | |
| 5,272,135 A | 12/1993 | Takruri | |
| 5,358,708 A | 10/1994 | Patel | |
| 5,372,808 A | 12/1994 | Blatt et al. | |
| 5,431,909 A | 7/1995 | Stewart, II | |
| 5,488,034 A | 1/1996 | McGregor et al. | |
| 5,503,827 A | 4/1996 | Woog et al. | |
| 5,609,868 A | 3/1997 | Lowther et al. | |
| 5,691,312 A | 11/1997 | Paques | |
| 5,711,944 A | 1/1998 | Gilbert et al. | |
| 5,723,121 A | 3/1998 | Takenaga et al. | |
| 5,738,846 A | 4/1998 | Greenwald et al. | |
| 5,762,923 A | 6/1998 | Guenter et al. | |
| 5,849,282 A | 12/1998 | Kawai et al. | |
| 5,858,001 A | 1/1999 | Tsals et al. | |
| 5,908,621 A | 6/1999 | Glue et al. | |
| 5,919,757 A | 7/1999 | Michaelis et al. | |
| 5,972,331 A | 10/1999 | Reichert et al. | |

FOREIGN PATENT DOCUMENTS

DE 3 723 781 1/1988
EP 0 043 980 1/1982

(Continued)

OTHER PUBLICATIONS

Anik et al., "Adsorption of D-Nal(2)$^6$ LHRH, a decapeptide, onto glass and other surfaces," *International Journal of Pharmaceutics*, 16:181-190 (1983).

(Continued)

*Primary Examiner* — Vanessa L. Ford
*Assistant Examiner* — Bruce D Hissong
(74) *Attorney, Agent, or Firm* — Ropes & Gray LLP

(57) ABSTRACT

Liquid interferon compositions having a pH between 4.0 and 7.2 are described. The compositions comprise interferon-beta and a stabilizing agent at between about 0.3% and 5% by weight which is an amino acid selected from the group consisting of acidic amino acids, arginine and glycine. If needed, salt is added to provide sufficient ionic strength. The liquid composition has not been previously lyophilized or previously cavitated. The liquid is preferably contained within a vessel having at least one surface in contact with the liquid that is coated with a material inert to adsorption of interferon-beta. A kit for parenteral administration of a liquid interferon formulation and a method for stabilizing liquid interferon compositions are also described.

29 Claims, 3 Drawing Sheets

FOREIGN PATENT DOCUMENTS

| | | |
|---|---|---|
| EP | 0 082 481 | 6/1983 |
| EP | 0 163 111 | 12/1985 |
| EP | 0 168 008 | 1/1986 |
| EP | 0 270 799 | 6/1988 |
| EP | 0 284 249 | 9/1988 |
| EP | 0 294 127 | 12/1988 |
| EP | 0 307 097 | 3/1989 |
| EP | 0 367 667 | 5/1990 |
| EP | 0396777 | 11/1990 |
| EP | 0 456 113 | 11/1991 |
| EP | 0 588 255 A1 | 3/1994 |
| EP | 0 736 303 | 10/1996 |
| EP | 0 697 887 | 11/1998 |
| EP | 1 017 413 | 7/2000 |
| JP | 59-025364 | 2/1984 |
| JP | 59-181224 | 10/1984 |
| JP | 2-111729 | 4/1990 |
| JP | 2-124832 A | 5/1990 |
| JP | 02223530 | 9/1990 |
| JP | 06-098921 | 4/1994 |
| JP | 06-271478 | 9/1994 |
| WO | WO 88/09674 | 12/1988 |
| WO | WO 89/02750 | 4/1989 |
| WO | WO 89/04177 | 5/1989 |
| WO | WO 89/05158 | 6/1989 |
| WO | WO 91/16038 | 10/1991 |
| WO | WO 94/26302 | 11/1994 |
| WO | WO 95/03285 | 2/1995 |
| WO | WO 95/31213 | 11/1995 |
| WO | WO 96/11018 | 4/1996 |
| WO | WO 96/30041 | 10/1996 |
| WO | WO 98/28007 | 7/1998 |
| WO | WO 2006/053134 A2 | 5/2006 |

OTHER PUBLICATIONS

Fransson et al., "Oxidation of human insulin-like growth factor I in formulation studies: kinetics of methionine oxidation in aqueous solution and in solid state," *Pharmaceutical Research*, 13:1252-1257 (1996).

Hanson et al., "Introduction to formulation of protein pharmaceuticals," *Chapter 7—Stability of Protein Pharmaceuticals, Part B: In Vivo Pathways of Degradation and Strategies for Protein Stabilization, Plenum Press*, New York, 209-225 (1992).

Manning et al., "Stability of protein pharmaceuticals," *Pharmaceutical Research*, 6:903-918 (1989).

Mulkerrin et al., "pH dependence of the reversible and irreversible thermal denaturation of γ interferons," *Biochemistry*, 28:6556-6561 (1989).

Muranaka et al., "Studies on safely problem by skin tests using human beta interferon preparation," *Journal of Interferon Research*, 4:115-122 (1984).

Wang et al., "Review of excipients and pH's for parenteral products used in the United States," *Journal of Parenteral Drug Association*, 34:452-462 (1980).

Wang et al., "Parenteral formulations of proteins and peptides: stability and stabilizers," *Journal of Parenteral Science & Technology*, 42:S4-S26 (1988).

Cleland et al., "The Development of Stable Protein Formulations: A Close Look at Protein Aggregation, Deamidation, and Oxidation", Critical Reviews in Therapeutic Drug Carrier Systems, vol. 10(4), pp. 307-377 (1993).

Jankowski et al., "Binding of Human Interferons to Immobilized Cibacron Blue F3GA: The Nature of Molecular Interaction", Biochemistry, vol. 15(23), pp. 5182-5187 (1976).

Kontsek, P., "Human Type I Interferons: Structure and Function", Acta Virologica, vol. 38, pp. 345-360 (1994).

Samudzi et al., "Crystal Structure of Recombinant Rabbit Interferon-γ at 2.7-Å Resolution", The Journal of Biological Chemistry, vol. 266(32), pp. 21791-21797 (1991).

Sulkowski et al., "Interaction of Human Interferons with Immobilized Hydrophobic Amino Acids and Dipeptides", The Journal of Biological Chemistry, vol. 251(17), pp. 5381-5385 (1976).

The IFNB Multiple Sclerosis Study Group. Interferon beta-1b is effective in relapsing-remitting multiple sclerosis. I. Clinical results of a multicenter, randomized, double-blind, placebo-controlled trial. Neurology, vol. 43; pp. 655-661 (1993).

Geigert et al., "Potency Stability of Recombinant (Serine-17) Human Interferon-β," Journal of Interferon Research, vol. 7, pp. 203-211 (1987).

Jacobs et al., "A phase III trial of intramuscular recombinant interferon beta as treatment for exacerbating-remitting multiple sclerosis: design and conduct of study and baseline characteristics of patients," Multiple Sclerosis, vol. 1, pp. 118-135 (1995).

Salmon et al., "Pharmacokinetics and Pharmacodynamics of Recombinant Human Interferon-β in Healthy Male Volunteers," Journal of Interferon and Cytokine Research, vol. 16, pp. 759-764 (1996).

\* cited by examiner

STABLE LIQUID INTERFERON-BETA FORMULATIONS

This application is a continuation of copending U.S. patent application Ser. No. 10/397,108, filed Mar. 24, 2003, which is a continuation of U.S. patent application Ser. No. 09/403,930, filed Oct. 28, 1999, which is a National Phase filing under 35 U.S.C. §371 of International Application PCT/US1997/023817, filed Dec. 23, 1997, which designates the United States, is published in English and claims priority under 35 U.S.C. §119(e) from U.S. Provisional Application 60/034,353, filed Dec. 24, 1996, all of which are hereby incorporated by reference herein in their entireties.

FIELD OF THE INVENTION

This invention relates to methods for stabilizing human interferon-beta and to stable, interferon-beta liquid formulations.

BACKGROUND OF THE INVENTION

Interferons are proteins having a variety of biological activities, some of which are antiviral, immunomodulating and antiproliferative. They are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. In most cases, interferons provide better protection to tissues and cells of the kind from which they have been produced than to other types of tissues and cells, indicating that human-derived interferon should be more efficacious in treating human diseases than interferons from other species.

There are several distinct types of human interferons, generally classified as leukocyte (interferon-alpha), fibroblast (interferon-beta) and immune (interferon-gamma), and a large number of variants thereof. General discussions of interferons can be found in various texts and monographs including: The Interferon System (W. E. Stewart, II, Springer-Verlag, N.Y. 1979); and Interferon Therapy (World Health Organization Technical Reports Series 676, World Health Organization, Geneva 1982), incorporated herein by reference.

The method of administering interferon is an important factor in the clinical application of this important therapeutic agent. Systemic administration of interferon by either intravenous, intramuscular or subcutaneous injection has been most frequently used with some success in treating disorders such as hairy cell leukemia, Acquired Immune Deficiency Syndrome (AIDS) and related Kaposi's sarcoma. It is known, however, that proteins in their purified form are especially susceptible to degradation. For interferon-beta, the primary mechanism(s) of interferon degradation in solution are aggregation and deamidation. The lack of interferon stability in solutions and other products has heretofore limited its utility.

Pharmaceutical interferon compositions for clinical use commonly contain interferon as a lyophilized (i.e., freeze-dried) preparation in combination with complex organic excipients and stabilizers such as nonionic surface active agents (i.e., surfactants), various sugars, organic polyols and/or human serum albumin. Lyophilized preparations have the disadvantage of requiring complex packaging since a separate supply of sterile water for injection is required. Moreover, lyophilized preparations require several manipulations prior to use, thus increasing the possibility of needle sticks and dropped components during preparation for injection. These manipulations are especially problematic for patient populations that exhibit muscle weakness and poor coordination, such as people with multiple sclerosis (MS). MS patients may self-administer interferons so that the availability of a dosage form that is much easier to administer than current lyophilized products represents important added value for the target patient population. Simple liquid formulations of interferon are highly desirable in order to avoid the reconstitution necessary when lyophilized preparations are used.

Liquid, non-lyophilized formulations containing interferons may also contain complex carriers such as human serum albumin, polyols, sugars, and anionic surface active stabilizing agents. See, for example, WO 89/10756 (Hara et al.—containing polyol and p-hydroxybenzoate).

SUMMARY OF THE INVENTION

This invention has solved the above problems with the discovery that human interferon-beta can be stabilized when placed in buffered solutions having a pH between about 4 and 7.2, the solutions containing an amino acid as a stabilizing agent and in some cases a salt (if the amino acid does not contain a charged side chain). The interferon-beta is not lyophilized but, once prepared from sources using methods known to the ordinarily skilled artisan, is included directly in the formulation of this invention.

Therefore, one aspect of the invention is a liquid composition comprising an interferon and a stabilizing agent at between about 0.3% and 5% by weight which is an amino acid selected from the group consisting of acidic amino acids, arginine and glycine. The liquid composition has not been previously lyophilized. Moreover, it is preferable that the liquid composition is contained within a vessel, such as a syringe, in which the vessel has a surface in contact with the liquid that is coated with a material inert to interferon such as silicone or polytetrafluoroethylene. Preferred compositions include interferon-beta, or a recombinantly produced interferon, in a buffer having a pH between about 4.0 and about 7.2. Other formulations of the invention include:

(1) a 20 mM acetate buffer at pH 5.0, the buffer not previously lyophilized, in which the buffer includes interferon-beta plus ingredients selected from (a) 150 mM arginine-HCl; (b) 100 mM sodium chloride and 70 mM glycine; (c) 150 mM arginine-HCl and 15 mg/ml human serum albumin; (d) 150 mM arginine-HCl and 0.1% Pluronic F-68; (e) 140 mM sodium chloride; (f) 140 mM sodium chloride and 15 mg/ml human serum albumin; and (g) 140 mM sodium chloride and 0.1% Pluronic F-68;

(2) a liquid at pH 5.0 that includes interferon-beta, 170 mM L-glutamic acid, and 150 mM sodium hydroxide, the liquid not previously lyophilized;

(3) a 20 mM phosphate buffer at pH 7.2, the buffer not previously lyophilized, wherein the buffer includes interferon-beta plus ingredients selected from: (a) 140 mM arginine-HCl; and (b) 100 mM sodium chloride and 70 mM glycine.

Another embodiment of the invention is a kit for parenteral administration of a liquid interferon formulation. The kit comprises a vessel containing a liquid formulation at a pH of between 4 and 6, the liquid comprising a pharmaceutically effective amount of interferon-beta that has not been previously lyophilized and an amino acid stabilizing agent about 5% by weight or less; and instructions for use.

Yet another embodiment of the invention is a liquid pharmaceutical composition suitable for parenteral administration to mammals consisting essentially of an effective amount of interferon-beta that has not been previously lyophilized in a buffer maintaining the pH within the range of 4.0 to 6.0, and an amino acid stabilizing agent at an appropriate ionic strength. The composition is contained within a storage vessel such as a syringe. Preferably, the storage vessel lacks an oxygen-containing/liquid interface (i.e, the interferon solution is not subjected to oxygen containing gas during preparation and storage). The interferon-beta essentially retains its antiviral activity during storage at a temperature of between about 2 degrees C. and about 25 degrees C. for a period of at least 3 months.

A process of the invention for stabilizing interferon-beta in liquid pharmaceutical compositions so that it essentially retains its physical stability during storage at a temperature of between about 2 and about 25 degrees C. for a period of at least 3 months, comprises admixing: a) an effective amount of interferon-beta; b) a buffer maintaining the pH within the range of 4.0 to 7.2 at an appropriate ionic strength; and c) an amino acid stabilizing agent, wherein the liquid has previously not been lyophilized and has not been subject to oxygen containing gas during preparation and storage.

The liquid formulations of the invention have many advantages over lyophilized formulations. The advantages include: (i) a smaller injection volume required for a liquid formulation will induce less discomfort than a larger volume; (ii) replacement of complex excipients with simple amino acids makes it possible to monitor finished product quality more closely; (iii) packaging is greatly simplified due to elimination of the need for a separate supply of water for injection (WFI) and separate syringe and vial; (iv) dosing accuracy may be improved due to fewer liquid transfers; and (v) product safety is improved because the simpler administration decreases the chance of needle punctures and dropped components during preparation for injection.

Therefore, an object of the present invention is to provide a biologically active, stable liquid formulation of interferon-beta for use in injectable applications.

Another object of this invention is to provide a formulation which does not require prior lyophilization of a interferon-beta composition.

It is another object of this invention to prevent loss of stability in an interferon-beta liquid formulation by: a) avoiding cavitation and/or head space formation during preparation of the liquid composition, or b) storing the liquid formulation with a head space that consists of an inert gas such as argon or nitrogen.

Still another object of this invention is to provide a liquid formulation permitting storage for a long period of time in a liquid state facilitating storage and shipping prior to administration. Another object of this invention is to provide a liquid formulation which is easily made and administered having eliminated lyophilization and reconstitution steps.

A further object of the invention is the use of simple amino acids as alternate stabilizers besides commonly-used serum albumin, making it easier to monitor product quality.

Yet another object of this invention is to provide a pharmaceutical composition containing non-lyophilized interferon-beta that can be produced less expensively.

Other advantages of the invention are set forth in part in the description which follows, and in part, will be obvious from this description, or may be learned from the practice of this invention. The accompanying drawings, which are incorporated in, and constitute a part of, this specification, illustrates and together with this description, serves to explain the principle of the invention.

DETAILED DESCRIPTION OF THE INVENTION

Figure 1:
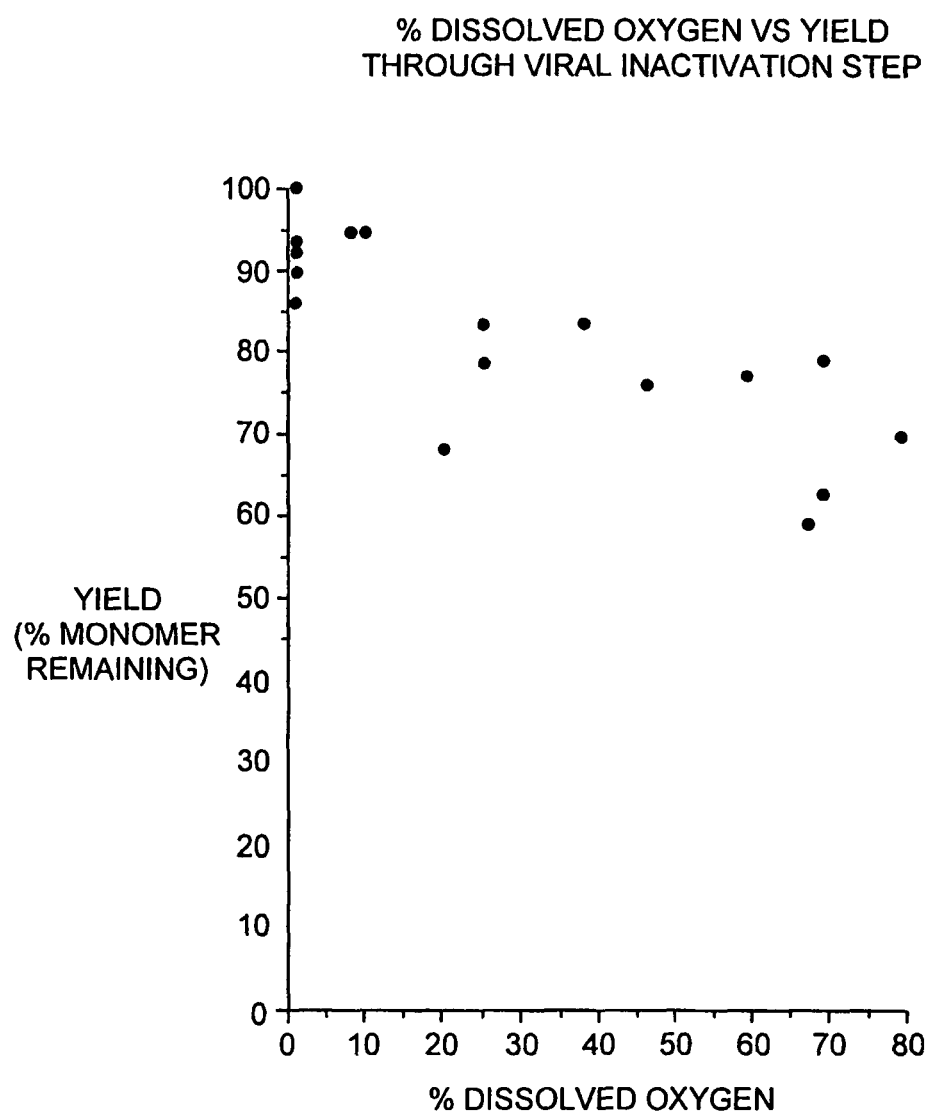
FIG. 1 is a graph showing the percentage of interferon-beta monomer remaining in bulk process liquid as a function of the percentage dissolved oxygen in the liquid.

The present invention overcomes the problems and disadvantages associated with current strategies and designs and provides a simple method for stabilizing interferon and a simple interferon formulation with enhanced storage stability. The invention is based, in part, on our discoveries that:

a) interferon-beta is particularly unstable and aggregates when contacted with oxygen that is either actively bubbled through the liquid or statically contacted as in a head space;

b) interferon-beta liquid preparations lacking a carrier such as human serum albumin are particularly susceptible to adsorption (i.e., either chemical reaction or physical linkage) to the glass surfaces; and c) interferon-beta aggregates at low ionic strength, requiring an ionic milieu for stability in the aqueous state.

The invention is therefore directed to methods for stabilizing human interferon-beta that avoid these pitfalls, and to the resulting liquid formulations of stabilized interferon-beta.

A. Definitions

The term "buffer" refers to solutions of a weak acid and a salt containing the anion of the acid, or solutions of a weak base and its salt. In particular, the term "acetate" when used in this specification (see also Table I, infra) refers to a buffer system preferably containing sodium acetate and acetic acid and the term "phosphate" refers to a buffer system preferably containing dibasic and monobasic sodium phosphate hepta- and mono-hydrate, respectively. Moreover, those solutions in Table II (infra) containing an acidic amino acid in combination with sodium hydroxide, albeit not conventionally considered to be buffers as this term is known in the art, are nonetheless included within the definition herein.

The term "excipient" refers to any compound added during processing and/or storage to a liquid formulation for the purpose of altering the bulk properties, improving stability and/or adjustment of osmolality.

The term "stabilizing agent" refers to an excipient that improves or otherwise enhances stability.

The term "stability" has by necessity a functional definition and means the relative temporal constancy of interferon activity such as anti-viral activity and/or interferon structure.

The term "cavitated" refers to any liquid interferon formulation that, because of changes in pressure or physical agitation, has had contact with oxygen-containing bubbles (e.g., air) at least during its preparation and storage. The term "cavitation" also means that a oxygen-containing gas/liquid interface has been formed at some point during preparation, storage, and use of the liquid interferon formulation. The term "cavitated" also means that the dissolved oxygen levels in the liquid interferon formulations exceed about 10% of atmospheric equilibrium values at the temperatures typically encountered at least during preparation and storage.

The term "parenteral" as used herein includes subcutaneous, intravenous, intramuscular, intrasternal, intraperitoneal, ophthalmic, or intraspinal injection or infusion techniques.

The expression "pharmaceutically-acceptable salt" means any organic or inorganic addition salt which is relatively non-toxic and innocuous to a patient at concentrations consistent with effective activity so that the side effects ascribable to the salt do not vitiate the beneficial effects of the interferon.

An "effective amount" of a compound is that amount which produces a result or exerts an influence on the particular condition being treated. An "effective amount" also means that amount which produces a positive result (i.e., exerts an anti-viral effect) in the CPE test for anti-viral activity.

As used herein, a "pharmaceutically effective amount" of interferon means a percentage concentration of that agent known in the medical and pharmaceutical arts to be safe and effective in treating a particular condition.

"Isotonic to blood" (used interchangeably with "isotonicity") refers to a liquid interferon composition that has a sufficient concentration of components so that its osmotic behavior is substantially identical to blood, i.e., cells in contact with the formulation will substantially retain their shape and undergo substantially no net transfer of water by osmotic pressures.

"Poly-ionic species" (used interchangeable with "poly-electrolytic species") refers to a substance of high molecular weight that is an electrolyte and, when used in the formulations of this invention, maximizes ionic strength for a given osmolality. This definition is based on our finding that interferon-beta is stabilized by high ionic strength, but that total ionic strength is limited by the necessity for the solution to be isotonic to blood (See Example 7). A preferred way to maximize ionic strength for a given osmolality is to use an excipient that is a poly-ionic species.

A material that is "inert to interferon" means a material having at least the property of not physically and/or chemically reacting with interferon.

B Making Interferons

This invention is generally applicable to all types of interferon including natural interferon, interferon produced by recombinant DNA technology, and interferon produced by chemical synthesis or modification. Also, the invention can be used with crude, semi-purified and purified interferon from fibroblasts, leukocytes, lymphocytes or any other interferon-containing or producing tissues from humans or any other appropriate species. Most preferably, the invention is applicable to human fibroblast interferon (interferon-beta).

The most preferred interferon-beta is a recombinant form and recombinant DNA methods for producing proteins including the various interferons are known and are not intended to limit the invention in any way. See for example, U.S. Pat. Nos. 4,399,216, 5,149,636, 5,179,017 (Axel et al); 4,470,461 (Kaufman). Recombinant forms of interferon-beta have been produced. See, for example, European Patent 0 41313 (Fiers—expression of Interferon-beta); U.S. Pat. No. 4,966,843 (McMormick et al.—expression of interferon in CHO cells); U.S. Pat. No. 5,326,859 (Sugano et al.—DNA encoding interferon-beta); Interferon-beta can also be modified, either recombinantly or chemically and can be produced in serum-containing or serum-free media. Forms of interferon-beta may include variants such as cysteine-depleted mutants (U.S. Pat. Nos. 4,588,585 and 4,737,462: Mark et al.) and methionine-depleted mutants (EP 260 350—Wang et al.).

The primary amino acid sequence of the protein may be augmented by derivatization using sugar moieties (glycosylation) or by other supplementary molecules. Other modifications may take place through the post-translational processing systems of the host cell. Individual amino acid residues in the chain may be further modified by oxidation, reduction or other derivatization, and the protein may be cleaved to obtain active fragments. The exact chemical structure of a particular recombinant interferon-beta will therefore depend a several factors and is not intended to limit the scope of the invention. All such interferon-beta proteins included in the formulations described herein will retain their bioactivity when placed in suitable environmental conditions.

One method of producing recombinant interferon-beta is to culture Chinese hamster ovary (CHO) cells transfected with the human interferon-beta gene. Recombinant interferon-beta is secreted by CHO cells grown up in batch suspension culture containing fetal bovine serum. Cells may be grown in spinner flasks housed in a $CO_2$ incubator (5% $CO_2$) at about 35 degrees Celsius (hereinafter "C"). Multiple spinner flasks may be pooled and inoculated into fermenters of increasing size if scale-up is desired. Growth in a given fermenter is carried out for about six days at which time the active interferon-beta product accumulates in the culture medium. The culture may then be harvested and the cells removed from the product-containing medium by, for example, tangential flow filtration.

C. Purifying Interferons

Purification schemes for interferons are well characterized and available to those having ordinary skill in the art. Such methods include single- or multi-step procedures involving various chromatographic separation steps. See, for example, U.S. Pat. No. 5,015,730 (Friesen et al.—affinity chromatography and HPLC); U.S. Pat. No. 4,541,952 (Hosoi et al.—chelation chromatography).

An exemplary method involves exploiting the unusually hydrophobic and relatively basic nature of the interferon-beta molecule as well as its strong affinity for binding metal ions. See, for example, Knight and Fahey, "Human Fibroblast Interferon, an Improved Purification", *J. Biol. Chem.*, 256: 3609-3611 (1981) and Edy et al., "Purification of Human Fibroblast Interferon by Zinc Chelate Chromatography", *J. Biol. Chem.*, 232: 5934-5935 (1981), both of which are incorporated herein by reference.

Briefly, the capture and purification steps involve binding of interferon-beta to a series of Sepharose® columns (mfg. by Pharmacia Biotech) and elution with salts and a polyol. Once the final Sepharose eluate has been diluted and adjusted by lowering pH, the interferon-beta therein will bind to SP Sepharose® (Pharmacia Biotech). Most of the remaining proteins present in the column load are more basic in nature than monomeric interferon-beta and bind more tightly to the column than does the interferon. DNA and viruses partition from interferon-beta on this column. The column is then washed with a series of buffers containing sodium chloride.

The interferon product will now bind to a chelating Sepharose® (Pharmacia Biotech) column that has been previously charged with zinc. See Edy et al., supra. This column is operated under an oxygen-free atmosphere to protect the free sulfhydryl group in the molecule, as are all the subsequent steps. The purified interferon is acidified and held at low pH to inactivate any remaining viruses. After neutralization, the interferon is concentrated using cross flow filtration and then buffer exchanged into a neutral buffer solution. The buffer exchange process reduces the concentrations of zinc and organic compounds. Following this, the bulk interferon may be stored at −70 C prior to the formulation steps.

D. Formulating Interferons

In the exemplary purification method described above and after the first buffer exchange process, a second buffer exchange process is initiated except that the neutral buffer solution is replaced with a buffer solution between pH 4 and 7.2 that contains a stabilizing agent, described in more detail below. The resulting formulation containing interferon is referred to as a "process intermediate" and may be frozen for storage. See also Example 7.

If stored in a frozen state (under an atmosphere of an inert gas such as argon or nitrogen), it may then be thawed and pumped through a 0.22 micron filter into a tared vessel, preferably stainless steel, where the process intermediate is combined with a previously filter-sterilized diluent until the desired final product weight is achieved. The diluent consists of the same buffer that was used in the second buffer exchange process. The liquid final product is then filter sterilized under aseptic procedures, using for example, two 0.22 micron filters in series, and dispensed into a sealed vessel, preferably stainless steel, that contains an inert gas inlet, a de-gassing valve/filter combination, and an inflow/outflow dip tube. The final product is pumped through the dip tube and into the sealed vessel. Using an inert gas such as nitrogen, the final product is pressure transferred to the pump head of a device capable of aseptically filling sterile syringes.

Several methods of aseptically filling sterile syringes are available and the particular method used is not intended to limit the scope of the present invention. An exemplary method involves use of a HYPAK® autoclavable syringe filler (Becton Dickinson Pharmaceutical Systems, Franklin Lakes, N.J.). The syringes are autoclaved with tip caps in place. Generally, devices of this type incorporate a vacuum chamber that contains the syringes to be filled with interferon formulation. The chamber is placed in an aseptic environment. Each syringe lies vertically in the chamber with its open end being mated to a plunger pin, adapted to fit into the open end of the syringe barrel. The pin is designed to insert a stopper into the barrel to trap the liquid within. A small head space is left in the syringe after insertion. The chamber is evacuated and back-flushed with an inert, oxygen-free gas (e.g., argon, nitrogen) several times and when the final vacuum is reached, the pins are mechanically driven into the open syringe barrels a short distance and the stoppers are automatically inserted into the respective syringes. The chamber is then vented with filtered air to bring the pressure inside the chamber back to atmospheric levels. The amount of the vacuum will determine the size of the inert gas-containing head space.

In the particular system we use, the syringes are oriented vertically and held in place by a sprocket on a rotating disk. The syringes are first positioned under a needle which is inserted into the syringe. The needle flushes the syringe interior with an inert gas (e.g. nitrogen, argon). The needle then retracts out of the syringe. The syringe is then positioned under a second needle which is inserted into the syringe. This needle is attached to a pump which dispenses product into the syringe. The second needle then retracts out of the syringe. The syringe is then positioned under a third needle which is inserted into the syringe. A plunger (previously autoclaved) is blown into the syringe with an inert, oxygen free gas (e.g. nitrogen, argon), then the needle retracts out of the syringe. The plunger is positioned to leave a head space of inert gas between the top of the liquid and the bottom of the plunger.

1. The Excipient:

The excipient is preferably a poly-ionic species that maximizes ionic strength for a given osmolality, such as, for example, a polyelectrolyte that may include heparin or other polymeric species. As discussed in Example 4, interferon-beta is stabilized by high ionic strength, but total ionic strength is limited by the necessity for the solution to be isotonic to blood. A preferred way to therefore maximize ionic strength for a given osmolality is to use a poly-ionic species. Interferon-beta solutions of the invention are isotonic to blood (about 290 milliosmols/kilogram).

The most preferred stabilizing agent for the present invention is an amino acid that may include one of the following: any acidic amino acid (e.g., glutamic acid, aspartic acid) or an amino acid selected from arginine and glycine. Most preferably, the amino acid stabilizing agent is arginine which is incorporated as its acidic form (arginine-HCl) in pH 5.0 solutions. A preferred acidic amino acid is L-glutamic acid. Without wishing to be bound by any theory, the fact that poly-ionic excipients are preferred is probably why arginine and lysine (with 3 charged groups) stabilize interferon better than glycine (with 2 charged groups), which in turn stabilizes better than any of the uncharged species tested.

If the excipient is arginine-HCl, its concentration will range between 0.5% (w/v) to 5% and is most preferably 3.13% (equivalent to 150 mM arginine-HCl). If the excipient is glycine, its concentration will range between 0.50% (w/v) to 2.0% and most preferably 0.52% (equivalent to 66.7 mM to 266.4 mM, and most preferably 70 mM). If the excipient is glutamic acid, its concentration will range between 100 mM to 200 mM, and is most preferably 170 mM (equivalent to a w/v percent ranging from 1.47% to 2.94% and most preferably 2.5%).

We analyzed different excipients as a stabilizing agent for liquid formulations of interferon-beta using the pH buffer system of 50 mM sodium acetate and glacial acetic acid in combination with 100 mM sodium chloride, pH 5.0. Liquid interferon samples are either thermally stressed by incubation at 37 degrees C. for about 1 to 3 weeks or placed on a rotator for 1 to 3 days as a mechanical stress. Treated samples are evaluated for interferon-beta stability by the methods described in Example 1. As described in more detail in Example 7, the formulations buffered at pH 5.0 with sodium acetate containing an amino acid excipient (and optionally containing sodium chloride) show the best stability.

2. The Interferon

The preferred interferon is fibroblast interferon-beta, most preferably as recombinant human interferon-beta produced from mammalian cells. The recombinant human interferon-beta may contain a free sulfhydryl and at least one disulfide bond. A particularly preferred molecule contains one free sulfhydryl at position 17 and one disulfide bond between positions 31 and 141 per molecule. As is known to be the case with natural human IFN beta, N-glycosylation is expected at Asn-80. The range of concentration in the liquid formulations of the invention is from about 30 ug/ml to about 250 ug/ml. A preferred concentration range is 48 to 78 ug/ml and the most preferred concentration is about 60 ug/ml. In terms of International Standard values, the Biogen internal standard has been standardized to the WHO International Standard for Interferon, Natural #Gb-23-902-531, so that the range of concentration in IU (for a 0.5 ml injection volume) is from about 6 IMU to 50 IMU and the most preferred concentration is 12 IMU.

3. The Buffer:

The organic acid and phosphate buffers to be used in the present invention to maintain the pH in the range of about 4.0 to 7.2 and preferably from about 4.5 to about 5.5, and most preferably 5.0, can be conventional buffers of organic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) phosphate buffers (sodium phosphate monobasic/sodium phosphate dibasic) and acetate buffers (e.g., acetic acid-sodium acetate mixture, acetic acid-sodium hydroxide mixture, etc.).

In the Examples described below, we use different buffer concentrations and different pHs of sodium phosphate, sodium citrate, sodium succinate, sodium carbonate and sodium acetate for evaluation of the most appropriate buffer. Interferon-beta samples are either placed at 37 degrees C. for 6 days to 2 weeks or placed on a rotator for 7 to 9 hours in order to accelerate degradative processes. Chemical properties of the samples are then determined. The samples are analyzed by optical density, peptide mapping, Size Exclusion HPLC, reduced and non-reduced SDS-PAGE/Western blots, and isoelectric focussing/Western blots (IEF), all described below in Example 1. All experimental interferon-beta samples are compared to the starting interferon-beta material or to interferon-beta samples placed between 2 and 8 degrees C. Our data indicate that pH is the major factor that determines the stability of our interferon-beta samples and that samples between pH 4.0 and 5.0 are more stable than those of pH 7.0 or greater. See Example 2. Nevertheless, we were able to develop several interferon-beta formulations at physiological pH (pH 7.2). See Example 6.

4. Cavitation

Most free sulfhydryl residues in interferon-beta undergo oxidation at high pH (pH>8.0), the pH at which disulfide bonds undergo rearrangement. We have detected some aggregation of interferon-beta in our bulk intermediate by size-exclusion chromatography, non-reduced SDS-PAGE and laser light scattering. We have subsequently discovered that formation of aggregated interferon-beta may be dependent upon the level of dissolved oxygen. The process criteria that we have developed for ensuring that the liquid interferon-beta formulations are not cavitated include: (a) if possible, there should be no oxygen-containing gas/liquid interface present during preparation and storage; and/or (b) there should be no bubbles formed during preparation and storage; and/or (c) the levels of dissolved oxygen in the formulation should be kept below 10% of atmospheric equilibrium at the preparation and storage temperature. See Example 3.

5. Adsorption of Interferon to Surfaces

We also determined that interferon will adsorb to certain surfaces and its storage in a glass vessel requires that at least one surface of the vessel in contact with the interferon be coated or otherwise covered with a material that will prevent or substantially eliminate the adsorption. This surface may be chemically or physically inert to adsorption. Exemplary materials for this purpose are known to those of ordinary skill in the art and may include, for example, sprayed or baked silicone, polypropylene, or polytetrafluoroethylene (PTFE). We took our preferred 60 ug/ml liquid formulations (BG9589-1, 2, 3, and 4: summarized in Table 1, below) and filled them into 1 ml long, Type I glass syringes coated with sprayed silicone (Beckon Dickinson) and into 0.75 ml Type I glass vials. The samples are then analyzed by reverse phase HPLC (rpHPLC) for protein concentration determination. The data indicate that there was less protein in solution in those samples that were filled into the glass vials as compared to the silicone-coated prefilled syringes. See Example 5.

6. Preferred Formulations

We performed kinetic analysis of protein stability using the four liquid formulations whose final concentrations are shown below in Table 1, each containing 60 ug/ml interferon-beta. Alternate formulations, some containing surfactants such as Pluronic F68 (mfg. by BASF) are given in Table 2.

TABLE 1

Preferred Formulations

| pH SYSTEM | EXCIPIENT | FINAL pH |
|---|---|---|
| 20 mM acetate | 150 mM arginine-HCl | 5.0 ("BG9589-1") |
| 20 mM acetate | 70 mM glycine<br>100 mM sodium chloride | 5.0 ("BG9589-2") |
| 20 mM phosphate | 140 mM arginine-HCl | 7.2 ("BG9589-3") |
| 20 mM phosphate | 70 mM glycine<br>100 mM sodium chloride | 7.2 ("BG9589-4") |

All formulation constituents are USP-grade materials. The detailed compositions are:

| Ingredient (as raw materials) | Amount | |
|---|---|---|
| BG9589-1 | | |
| Arginine-HCl, USP | 15.8 | mg |
| Glacial acetate acid, USP | 0.167 | mg |
| Sodium acetate trihydrate, USP | 0.972 | mg |
| Interferon-beta | 30 | ugm |
| Water for Injection, USP | 0.5 | ml |
| BG9589-2 | | |
| Glycine, USP | 2.628 | mg |
| Glacial acetate acid, USP | 0.185 | mg |
| Sodium acetate trihydrate, USP | 0.932 | mg |
| Interferon beta-1a | 30 | ugm |
| Water for Injection, USP | 0.5 | ml |
| Sodium Chloride | 2.922 | mg |
| BG9589-3 | | |
| Arginine-HCl, USP | 14.725 | mg |
| Sodium phosphate dibasic-7H20 | 2.332 | mg |
| Sodium phosphate monobasic-1 H20 | 0.359 | |
| Interferon beta-1a | 30 | ug |
| Water for Injection, USP | 0.5 | ml |
| BG9589-4 | | |
| Sodium phosphate dibasic-7H20 | 1.984 | mg |
| Sodium phosphate monobasic-1 H20 | 0.359 | mg |
| Interferon beta-1a | 30 | ug |
| Glycine | 2.628 | mg |
| Sodium Chloride | 2.922 | mg |
| Water for Injection, USP | 0.5 | ml |

TABLE 2

Alternate Formulations

| pH SYSTEM | EXCIPIENT | FINAL pH |
|---|---|---|
| 20 mM acetate | 150 mM arginine-HCl and<br>15 mg/ml human serum<br>albumin | 5.0 |

TABLE 2-continued

Alternate Formulations

| pH SYSTEM | EXCIPIENT | FINAL pH |
|---|---|---|
| 20 mM acetate | 150 mM arginine-HCl and 0.1% Pluronic F-68 | 5.0 |
| 20 mM acetate | 140 mM sodium chloride | 5.0 |
| 20 mM acetate | 15 mg/ml human serum albumin 140 mM sodium chloride | 5.0 |
| 20 mM acetate | 0.1% Pluronic F-68 140 mM sodium chloride | 5.0 |
| 170 mM L-glutamic acid, 150 mM sodium hydroxide | 15 mg/ml human serum albumin | 5.0 |
| 170 mM L-glutamic acid, 150 mM sodium hydroxide | 0.1% Pluronic F-68 | 5.0 |

Other materials may be incorporated into the formulations of this invention. These may include the following preservatives, where all preferred percentages are w/v: phenol (about 0.2%); methylparaben (0.08%); propylparaben (0.008%); m-cresol (0.1%); chlorobutanol (0.25%); benzyl alcohol (0.1%); and thimerosal (0.1%). Based on analyses to determine protein aggregation and deamidation (data not presented), the most preferred preservatives are chlorobutanol and benzyl alcohol.

7. Kits for Parenteral Administration

Preferred embodiments of the invention include a packaged kit for parenteral administration of the present liquid formulations. The package may include syringes pre-filled with the liquid formulations of the invention, several alcohol swabs, at least one needle, one or more adhesive bandages and directions for use. It will also appreciated that the present liquid formulations of the invention may be used with conventional needleless-injection systems.

E. Using Interferons

The interferon formulations of this invention have antiviral activity. See Example 7. For clinical use, the amount of interferon which is administered in any particular case, as well as the frequency at which the interferon is administered, depends upon such factors as the type of interferon used, the disease being treated, and the patient's response to interferon treatment.

A preferred use of the liquid compositions of the invention is for the treatment of relapsing multiple sclerosis. Lyophilized (i.e., reconstituted) liquid formulations of natural interferon-beta and recombinant interferon-beta have been administered to patients suffering from relapsing multiple sclerosis. See Jacobs et al., *Annals of Neurology* 39: 285-294 (March 1996) and references cited therein and Jacobs and Munschauer, "Treatment of multiple sclerosis with interferons" (pp. 223-250) in Treatment of multiple sclerosis: trial design, results and future perspectives, (R. A. Rudnick et al., eds), London: Springer, 1992. Use of the liquid formulations described herein for treating multiple sclerosis follows the same protocols and measures the same primary outcome variables as described in the Jacobs et al. paper, supra.

One way to assess the utility of the present liquid formulations is to perform a toxicology study and assess tissue irritation associated with administration of the liquid formulation. We have performed a toxicology study of the present liquid formulations in rabbits. See Example 8.

The following examples are offered to illustrate embodiments of the invention, but should not be viewed as limiting the scope of the invention.

Example 1 Assay Methods

Several well-characterized methods are used to determine the physico-chemical properties of the interferon-beta in our liquid formulations and these methods may be used to monitor properties of other interferons as well.

The presence/absence of insoluble aggregate is monitored by measuring the absorbance at 320 nm and transmittance at 580 nm. The concentration of soluble protein is determined by either measurement of absorbance at 278-280 nm (with an extinction coefficient of 1.5) or by reverse-phase high performance liquid chromatography (HPLC) using known concentrations of interferon-beta spiked in the formulation buffer as standards. The liquid formulation samples are centrifuged prior to assay. The soluble aggregate percentage is determined by separating aggregates from interferon-beta monomer by size exclusion chromatography on a TSK-Gel® G2000SWXL column (Toso Haas, Montgomeryville, Pa.). The peak areas monitored at 280 nm are used to calculated the percentage soluble aggregate.

The stability of the peptide backbone is confirmed by sodium dodecyl sulfate polyacrylamide gel electrophoresis (SDS-PAGE). Interferon-beta is reduced with mercaptoethanol in the presence of sodium dodecyl sulfate before being submitted to electrophoresis on a 10-20% gradient gel (MiniPlus Sepragel®, Integrated Separation Systems, Natick, Mass.). The proteins are then transferred electrophoretically to a nitrocellulose membrane and developed by immunodetection using anti-interferon-beta antibody and goat anti-mouse antibody coupled to horseradish peroxidase. See, for example, Gel Electrophoresis of Proteins, A Practical Approach, 2nd edition, B. D. Hames and D. Rickwood, IRL Press.

The change in the net surface charge, caused by deamidation and other chemical changes, is monitored by isoelectric focusing on a polyacrylamide gel (IEF 3-10 MiniPlus Sepragel®, Integrated Separation Systems). See, Gel Electrophoresis of Proteins, A Practical Approach, id.

Methionine oxidation, asparagine deamidation and other possible chemical changes are also monitored by peptide mapping. Interferon-beta is digested with Endoproteinase Lys-C (Wako Pure Chemicals) in the presence of dithiothreitol and the resulting peptide fragments are separated by reverse-phase HPLC. See generally, Kalgahtgi, K., & Horvath, C. "Rapid Peptide Mapping by High Performance Liquid Chromatography", J. Chromatography 443, 343-354 (1988).

The N-linked oligosaccharide profile is determined by using a Fluorophore-Assisted-Carbohydrate-Electrophoresis (FACE®) system by Glyko, Inc. (Novato, Calif.). The asparagine linked (N-linked) oligosaccharides are released from the glycoprotein using the enzyme Peptide N-glycosidase F, then labeled with a fluorophore at the reducing termini by reductive amination, separated and then quantified on a polyacrylamide gel.

Antiviral activity of interferons is determined by a number of methods such as those described more fully in: W. E. Stewart II, The Interferon System, Springer-Verlag (2d Ed. 1981). The Cytopathic Effect Inhibition Assay (CPE) is particularly useful for determining interferon antiviral activity. Our preferred method is described in WHO Technical Report Series No. 725, Annex 1, (1985), incorporated herein by reference. Briefly, this CPE method is initiated by preparing a working stock of interferon-beta standard that has been previously calibrated against a WHO reference standard. This stock is prepared in D-MEM+ medium containing 10% fetal bovine serum and 4 mM L-glutamine at a concentration of 10,000 units (U) per ml. On the day of assay, standard, control and samples are diluted into D-MEM+ in three separate dilution series: a) starting at 32 U/ml followed by 2-fold dilutions; b) starting at 12 U/ml followed by 1.5-fold dilutions; and c)

starting at 6 U/ml followed by 1.2-fold dilutions. Fifty microliters of the dilutions are added in columns to the wells of 96-well microtiter plates, one plate per dilution series. Next, A549 cells (ATCC Catalog Number CCL-185, Rockville, Md.) in D-MEM+ are added to each well at $5 \times 10^5$ cells/ml, 50 micro liters per well, effecting a two-fold dilution of both cells and interferon-beta. The cells and interferon are incubated at 37 degrees C. in 5% carbon dioxide for 15 to 20 hours. The plate contents are shaken into a bleach bucket and 100 microliters EMC (encephalomyocarditis) virus at appropriate dilution in media are added to each well. The virus and cells are incubated at 37 degrees C. and 5% carbon dioxide for 30 hours. The plate contents are shaken into a bleach bucket, and 0.75% crystal violet dye is added to the plates. After 5 to 10 minutes, the plates are washed with distilled water and allowed to dry. Each assay plate includes cell growth control wells containing neither interferon nor EMC, virus control wells containing EMC and cells but no interferon, and a dilution series of interferon standard.

Plates are examined visually to determine the last well in each column with viable cells (>25% confluent purple staining). The detection limit is determined as the lowest concentration of standard which protects from virus cytotoxicity. The sample dilution in the last positive well is multiplied by the detection limit determined for the standard and the sample dilution factor to obtain the interferon activity (MU/ml) in the sample. Results from each plate are transformed to log units for determination of geometric mean and calculation of 95% confidence intervals.

Example 2

Choice of Buffer System

We prepared three sets of buffers containing between nine and 10 different components for each set. Set I contains a series of sodium phosphate and/or 100 mM sodium chloride solutions between pH 4.0 and 7.2. Set II contains an additional series of sodium citrate buffers between pH 4.0 and 7.0. Set III contains a series of sodium succinate, sodium acetate and sodium carbonate buffer solutions, all combined with 100 mM sodium chloride, having pH values ranging from 4.0 to 7.2. Two other solutions replaced the sodium chloride with 50 mM sodium sulfate at a pH of 4.0 and 7.2.

Thawed, bulk interferon-beta is dialyzed into different buffers overnight at 2-8 degrees C. with at least two buffer exchanges, then sterile filtered prior to use. Protein concentrations are determined by absorbance at 278 nm (with extinction coefficient of 1.5 $mg^{-1}$ $ml \cdot cm^{-1}$) and all samples contained 140 ug/ml or 150 ug/ml interferon-beta. Samples are filtered and split into four sets by partially filling 2.2 ml eppendorf tubes. One set is placed at 2-8 degrees C.; one set was placed at 37 degrees C. for 6 days to two weeks; another set is placed on a rotator for 7 to 9 hours; and the final set is used as the zero-time control. Percentage loss of protein due to insoluble aggregates is calculated by the loss of the protein concentration during various treatments divided by the starting concentration.

Results:

The percentage protein loss by insoluble aggregates is calculated as loss of protein concentration divided by the starting protein concentration. A statistical analysis of all the data indicates that the interferon samples in buffers of pH 4.0 and 5.0 had a lower percentage loss of protein due to aggregation than those of higher pH. Interferon samples incubated at 37 degrees C. and pH 4.0 and 5.0 lost between about 10% and 15% due to aggregation. At pH values greater than 6.0, losses increased up to 40-50%. We also determined that the interferon samples have more soluble aggregates at pH values greater than 6.0. Moreover, we have determined by peptide mapping that as pH increases from 4.0 to 7.2, there is a substantially linear increase in the amount of interferon that is deamidated; at pH's 7.0 and higher, greater than 85% of interferon is deamidated during the study. We measured the isoelectric point (pI) of the protein species in the sample (i.e., that pH at which the protein does not migrate in an electric field and the mean charge on the protein is zero) with IEF/Western blots and the blots show extra pI bands of the samples in sodium citrate and a shifting of band intensity for samples in sodium succinate. Phosphate has no buffering capacity at pH 5.0. Sodium acetate with sodium chloride at pH 5.0 showed no change in banding pattern or intensity.

Example 3

The Effect of Cavitation

During our pH screening experiments described in Example 2, we discovered that the head space of the storage tubes appears to be critical for loss of protein of some of the samples. With 1.5 ml of the samples in 2.2 ml volume tubes, no loss of protein was observed. On the contrary, 1.2 ml of sample produced significant increase in aggregates. This is consistent with our observations that formation of aggregated interferon-beta during the viral inactivation step of the purification process is dependent on the level of dissolved oxygen during this step.

In brief, the viral inactivation step involves adjusting the pH of the chelating Sepharose eluate (see Section C) from 7.85+/−0.25 to between 2.5 to 3.5 with 15% phosphoric acid, holding the acidified eluate for 120-135 minutes, and then readjusting the pH to 6.7+/−0.7 with 0.5 N sodium hydroxide. All steps are performed at 2-8 degrees C. We designed a study to determine if a relationship exists between formation of interferon-beta aggregates in this step and the amount of dissolved oxygen.

Material and Methods

Eluate from the chelating Sepharose column is divided into 50 ml or 100 ml aliquots and placed into 100 ml spinner flasks. To each flask, 1 ml of argon-sparged 15% phosphoric acid is added. The flask is then gently stirred for about 2 minutes, and held without stirring for about 2 hours at 2-8 degrees C. Following this hold period, 6.5 ml of argon-sparged sodium hydroxide is added and the sample assayed by size-exclusion chromatography at various times. Dissolved oxygen within the liquid is measured continuously with an oxygen probe (Orion, Model 860) and recorded at the time of base addition. For samples with dissolved oxygen levels equal to or less than 10%, argon gas is swept through the reaction vessel head space.

Results: Data are presented in FIG. 1 which reveal a clear relationship between the amount of dissolved oxygen present at the time of sodium hydroxide addition and the yield of interferon-beta monomer through the virus inactivation step. The yield values obtained at dissolved oxygen concentrations less than or equal to 10% are significantly different from all other yields at other oxygen concentrations. We also characterized the aggregate (data not presented here) and determined that its specific activity is reduced about 30-40 fold from the bulk intermediate. We also determined that greater than about 90% of the aggregate is resistant to SDS denaturation under non-reducing conditions, suggesting a covalent cross-linkage. Under reducing conditions (2% beta-mercaptoethanol) the aggregate collapses to the monomer, suggesting cross-linkage that involves disulfide bonds.

Example 4

Choice of Excipient

A series of interferon-beta (60 ug/ml) formulations containing different excipients are prepared in a preferred pH 5.0 buffer containing 50 mM sodium acetate and 100 mM sodium chloride. The excipients include glycine, arginine-HCl, lysine-HCl, sucrose, glycerin, PEG3350, glutathione and Pluronic F-68. Interferon-beta bulk intermediate is dialyzed into 50 mM sodium acetate and 100 mM sodium chloride, pH 5.0 overnight at 2-8 degrees C. with at least two buffer exchanges, then filtered prior to use. Interferon-beta concentrations are determined by absorbance at 278 nm with background subtraction. Ml samples are diluted to final interferon concentrations of about 60 ug/ml. All prepared samples are filtered, two milliliters are transferred to 4 ml glass vials (non-siliconed), the head space sparged with argon and the vials sealed. Sets of samples are placed at 2-8 degrees C. and 37 degrees C. for periods up to two weeks. Other samples are mechanically stressed by rotating them at room temperature for 3 days.

Samples are analyzed according to the procedures of Example 1. In addition, the percentage of dissolved oxygen in the formulations is measured by a Ciba-Corning Model 248 blood gas analyzer. The "experimental" value is the oxygen partial pressure (mm Hg) of the samples minus that of the nitrogen purged buffer blank and the "control" value is the partial pressure of oxygen in the buffer blank stored at room temperature minus the oxygen partial pressure of the nitrogen purged buffer blank. The percentage dissolved oxygen ("experimental"/"control") is always less than 30%.

Results:

IEF/Western blots and SDS-PAGE/Western blots of samples incubated at 37 degrees C. for two weeks indicate band shifting and loss of intensity as well as the presence of interferon multimers in samples containing PEG3350 and glutathione. After an additional week at 37 degrees C., glycerin excipient shows one extra band in our blots. Sucrose excipient shows loss of band intensity. This initial screening procedure allowed us to consider in more detail arginine-HCl, glycine, sodium chloride and mannitol for further studies.

Example 5

Adsorption of Interferon

Thawed bulk interferon-beta is dialyzed to BG9589-1, 2, 3 and 4 (see Table 1) overnight at 2-8° C. with at least two buffer exchanges, then filtered prior to use. The protein concentrations are determined by absorbance at 280 nm (with extinction coefficient of 1.5 $mg^{-1}$ $ml \cdot cm^{-1}$). All the samples are diluted to final concentrations of approximately of 60 ug/ml. The diluted samples are filtered and filled either 0.5 ml into triplicate, 1.0 ml long, sprayed silicon BD syringes (Type I glass) with nitrogen flushed headspace or 0.75 ml into triplicate, 0.75 ml Type I glass vials with argon flushed headspace. Protein concentrations are determined by reverse phase HPLC (Example 1).

Results:

Table 3 below lists the protein concentrations that were determined by reverse phase HPLC. The data indicate that there is less protein for the samples that were filled into the glass vials as compared to the silicon coated prefilled syringes. Thus, siliconized syringes are used for the liquid formulation of interferon-beta.

TABLE 3

|  | Glass vial (ug/ml) (S.D) | Siliconized Syringes (ug/ml) (S.D) |
|---|---|---|
| BG9589-1 | 59.3 (2.6) | 63.3 (2.5) |
| BG9589-2 | 58.3 (0.7) | 61.7 (0.1) |
| BG9589-3 | 56.4 (0.4) | 58.8 (1.1) |
| BG9589-4 | 55.5 (0.7) | 59.3 (0.5) |

Example 6

Formulations at Physiological pH

Ionic Strength/Phosphate. We carried out initial studies in phosphate/sodium chloride, pH 7.2 buffer systems of varying buffer component concentrations in which the phosphate concentration varied between 10, 50 and 75 mM with an ionic strength (defined by $I=\Sigma c_I z_I^2$, where $c_I$ and $z_I$ are the molar concentration and valence charge of ionic species I, respectively) of 0.2, 0.4 and 0.6, adjusted by addition of sodium chloride.

We used a full factorial design on the variables of phosphate concentration (10, 50 and 75 mM) and ionic strength (I=0.2, 0.4, and 0.6). Compositions of sodium phosphate monobasic, sodium phosphate dibasic and sodium chloride (to achieve the desired ionic strength) in the buffers are calculated using a spreadsheet adapted from Ellis and Morrison, "Buffers of Constant Ionic Strength for Studying pH-dependent Processes", *Methods Enzymol.* 87: 405-426 (1982). The equations allowed determination of requisite amounts of each buffer component for specified pH, phosphate concentration and ionic strength. Each of the nine solutions used in the factorial experiment is obtained by buffer exchange of interferon-beta bulk intermediate through Pharmacia PD-10 desalting columns. The pHs of all resulting solutions are at 7.20+/−0.15. Concentrations are assayed by absorbance at 280 nm and then diluted to 150 ug/ml interferon-beta with the appropriate buffer. The resulting solutions are sterile filtered under argon through 0.22 micron filters, and 1.3 ml is aliquoted into 5 ml glass vials with an argon head space. Samples are incubated at 37 degrees C. for 6 days and run in triplicate. Samples are analyzed by percent transmittance at 580 nm, percent protein recovery, and IEF-PAGE/Western blots.

Results:

Analysis of percentage transmittance with respect to varying ionic strength shows a trend toward increasing transmittance (i.e, decreasing amounts of insoluble protein aggregates) with increasing ionic strength. Percent protein recovery data shows a similar trend although IEF-PAGE Western blots show no trend in deamidation with varying ionic strength so that all the samples are equally deamidated. Thus, after storage for six days at 37 C, samples tended to show less aggregation with decreasing phosphate concentration and increasing ionic strength. The results of the experiments on the percentage transmittance and percent recovery as a function of varying phosphate concentration (not presented here) show a weak trend towards decreasing % transmittance with increasing phosphate concentration, but an analysis of variance shows no significant difference in the means of samples with different phosphate concentrations. The percentage recovery data show improved protein recovery for lower phosphate concentrations (a significant difference at the 94% confidence level). IEF-PAGE Western blots display no discernible trend in deamidation with varying phosphate concentration.

Excipient/Salt Ratio. Preliminary studies (not shown) indicated that some excipients may require salts (e.g., sodium chloride) in order to maintain high ionic strength and in order to exhibit a stabilizing effect at pH 7.2. We designed a factorial study using excipients (glycine, lysine, arginine, sucrose and mannitol) and fraction of sodium chloride contributing to isotonicity ($f_{salt}$=0, 0.25, 0.75 and 1.0). The fraction is calculated by: $f_{salt}=O_{salt}/(O_{salt}+O_{excipient})$, where $O_{salt}$ and $O_{excipient}$ are the osmolalities in mOsm/kg of the sodium chloride and excipient, respectively, in the solution. Salt fraction provides a means of comparing salt effects across different excipients. All samples contained additives to isotonicity, with varying ratios of excipient:salt (as defined by $f_{salt}$).

Ten percent (w/v) stock solutions of each excipient in 20 mM phosphate, pH 7.2, are prepared, degassed, and sparged with argon. A stock solution of 250 mM sodium chloride, 20 mM phosphate, pH 7.2 is prepared, degassed and sparged with argon. Bulk interferon-beta intermediate is extensively dialyzed against argon-sparged 20 mM phosphate, pH 7.2 buffer. The resultant solution is assayed for interferon-beta concentration by absorbance at 280 nm and diluted with phosphate buffer and respective stock solutions of excipient and salt to achieve 60 ug/ml interferon-beta and the desired final salt and excipient conditions. The resulting samples are filter sterilized (0.22 micron) and filled into 1.0 ml Becton Dickinson sprayed silicone, Type I glass syringes (0.5 ml fill volume) with a nitrogen head space. Samples are stored at 40 degrees C.

At 6 days, arginine, glycine and sucrose samples are analyzed by absorbance at 320 and 280 nm, both before and after filtration through 0.22 micron filters. At 2 weeks, arginine, lysine and mannitol are similarly analyzed, along with IEF-PAGE, reducing SDS-PAGE and non-reducing SDS-PAGE. Control samples were stored at between 2 and 8 degrees C. and analyzed similarly.

Results:

The recovery of Interferon-beta 1a (as percentage of control) increases with increasing f salt for sucrose and mannitol, reaching a maximum recovery at $f_{salt}$=1 (130 mM sodium chloride). For arginine and lysine, recovery decreases with increasing $f_{salt}$. Maximum recovery for glycine formulations at pH 7.2 is reached at about $f_{salt}$=0.75.

This excipient screening study using a pH 7.2 phosphate buffer with various excipients such as glycine, lysine, arginine, mannitol and sucrose added to isotonicity, showed poor recovery for all non-charged excipients. The extent of deamidation was not affected by these additives. For instance, reducing and non-reducing SDS/PAGE indicate loss of non-glycosylated interferon-beta species in all formulations, and heavier multimer bands for isotonic sodium chloride alone and mannitol. In sum, there is a thus a strong correlation between the ionic character of the excipient and its ability to stabilize interferon-beta against aggregation in these buffer systems at physiological pH. Non-ionic additives such as sucrose and mannitol appear to offer no protection, or may actually promote protein loss at physiological pH. Sodium chloride, with a single charge per soluble species, performs better than either of mannitol or sucrose. Amino acids contain two charges per molecule at physiological pH. In the case of glycine, the zwitterionic nature of the molecule itself does not seem to be sufficient enough to stabilize interferon-beta. Arginine and lysine, each containing three charges per molecule, stabilize interferon-beta better than either sodium chloride alone or glycine/sodium chloride formulations.

Example 7

Stability and Kinetic Studies

Formulations are aseptically filled under an inert atmosphere, syringes incubated at a range of temperatures for varying time periods and syringe contents are analyzed. In brief, thawed bulk interferon-beta is dialyzed to BG9589-1, -2, -3 and -4 overnight at 2-8 degrees C. with a least two buffer exchanges Protein concentrations are determined by absorbance at 280 nm with an extinction coefficient of 1.5 ml/mg/cm. All samples are diluted to a final Interferon-beta-1a concentration of about 60 ug/ml. The four Interferon-beta-1a formulations of Table 1 are filtered and 0.5 ml are dispensed into 1.0 ml long, Becton Dickinson (BD) syringes whose interior surfaces were coated with baked silicone or with sprayed silicone. The samples were analyzed by OD, size exclusion HPLC (SEC), isoelectric focusing gel electrophoresis (IEF)/western blot, reduced sodium dodecyl sulfate polyacrylamide gel electrophoresis (SDS-PAGE)/western blot, peptide mapping, fluorophore assisted carbohydrate electrophoresis (FACE) and CPE bioassay. The head space in the syringe is nitrogen gas. The syringes are incubated at 2-8 degrees C., 25 degrees C., 33 degrees C. and 40 degrees C. for up to ninety days. Samples are analyzed according to the methods in Example 1.

Figure 2:
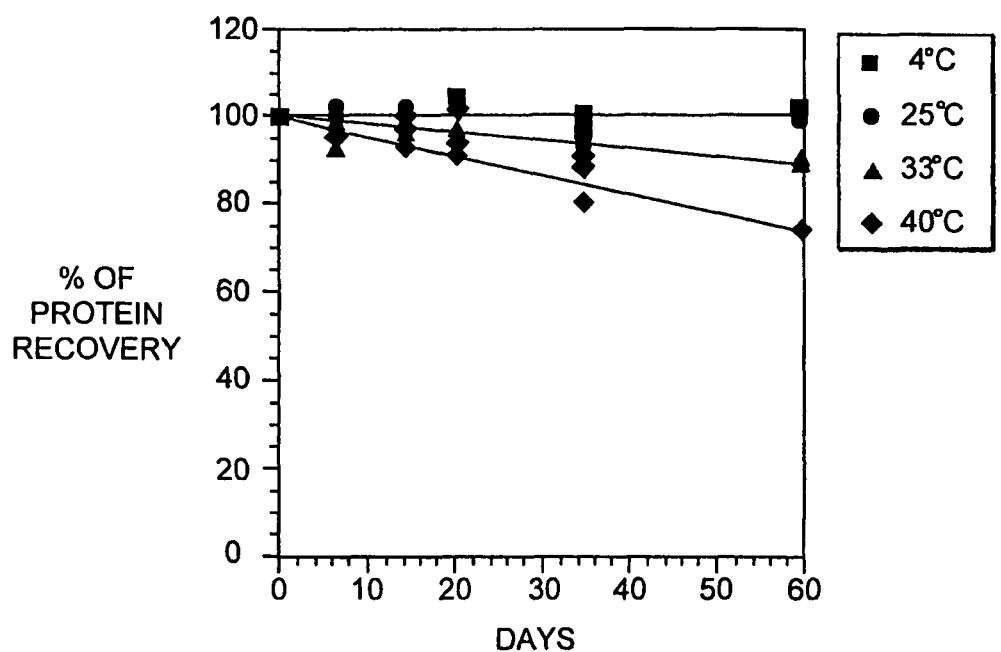
FIG. 2 is a graph showing the percentage of protein concentration normalized against that of starting material versus time for liquid formulation BG9589-1. Samples labeled "4° C." (closed squares) are incubated at between 2-8° C. Other samples are incubated at 25° C. (closed circles); 33° C. (closed triangles) and 40° C. (closed diamonds).
Figure 3:
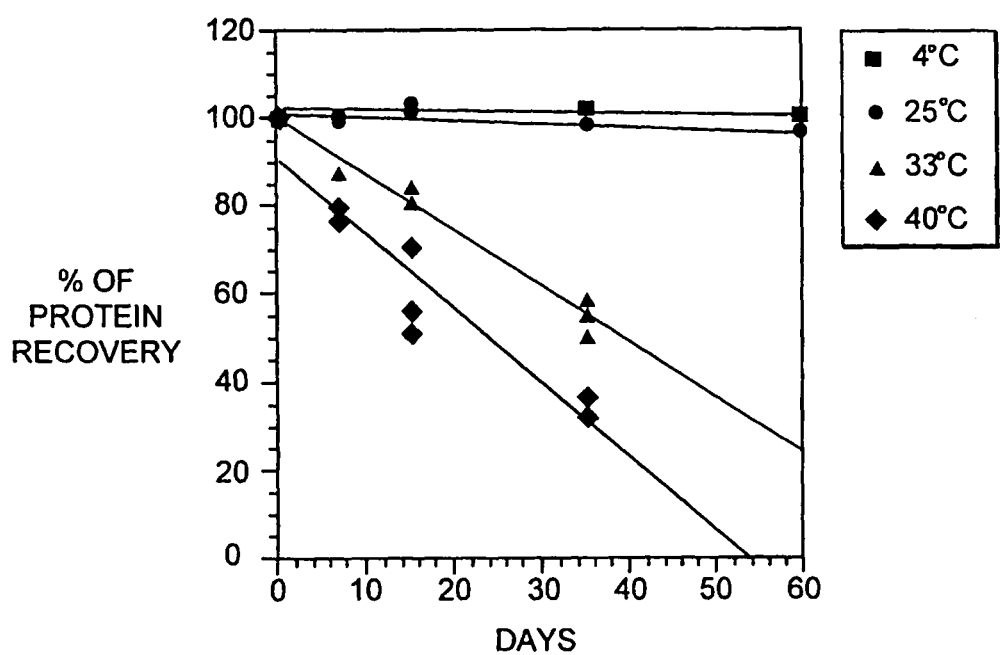
FIG. 3 is a graph showing the percentage of protein concentration normalized against that of starting material versus time for liquid formulation BG9589-3. Samples labeled "4° C." are incubated at between 2-8° C. Other samples are incubated at 25° C. (closed circles); 33° C. (closed triangles) and 40° C. (closed diamonds).

Results:

We analyzed protein concentrations of our samples, normalized against that of the starting material for periods up to ninety days at a variety of temperatures. FIG. 2 illustrates that BG9589-1 showed complete protein stability (no loss of protein) after 3 months incubation at temperatures ranging from 2-8 degrees C. (average 4 degrees C.) up to 25 degrees C. At a storage temperature (33 degrees C.) approaching body temperature, about 18% of the protein was degraded. At a storage temperature (40 degrees C.) exceeding body temperature, about thirty percent of protein was degraded at the end of 3 months. Substantially identical results were obtained for BG9589-2 (not shown). FIG. 3 illustrates results of 2 month storage tests on BG9589-3. Protein degradation was minimal at 4 through 25 degrees C. but was rapid at higher temperatures. Results for BG9589-4 are substantially identical to those in FIGS. 2 and 3. These data were confirmed using reduced SDS-PAGE/Western blots.

In the "baked" syringes, over the period of this study there are no detectable soluble aggregates. No significant changes are observed in protein concentration, CPE assay, percent Oxidized AP6 and carbohydrate profiles. There are no observable changes in the samples as seen by reducing SDS-PAGE/western blot and IEF/western blot. There is some increase in percent deamidation as compared to the starting time point. However, the bulk intermediate that was used to fill these syringes has 37% deamidation, which is higher than the 33.8% value of the material after being filled into the syringes. This latter, low value may be due to assay variability. In the "sprayed" syringes over the period of this study, there are also no detectable soluble aggregates. No significant changes are observed in protein concentration, CPE assay, percent deamidation, percent Oxidized AP6 and carbohydrate profiles. There are no observable changes in the samples as seen by reducing SDS-P-AGE/western blot and IEF/western blot. In short, results so far have shown that final product BG9589-1 is stable up to 3 months at 2-8 degrees C. in the "baked silicone" syringes, and 6 months at 2-8 degrees C. in "sprayed silicone" syringes.

We performed the antiviral CPE assay on formulations BG9589-1 and BG9589-2 (see Table 1) after syringes were aseptically filled. Reported activity values for both BG9589-1 and BG9589-2 are 12.0 MU/ml. The antiviral CPE assay was repeated after storage of the samples for up to 3 months at between 2-8 degrees C. The reported activity values for BG9589-1 are 11.6 MU/ml (n=8) with a 95% confidence interval of 10.2-13.3 MU/ml.

We also measured stability of the bulk intermediate material of BG9589-1 at 2-8 degrees C. for 5 months, and −70 degrees C. for 6 months. Samples of BG9589-1 from pilot diafiltration studies were analyzed by the methods of Example 1. Results so far have shown that in-process material of BG9589-1 is stable at 2-8 degrees C. for 5 months, and at −70 degrees C. for 6 months.

Over the period of this particular study, there are no detectable soluble aggregates. No significant changes are observed for percent deamidation and carbohydrate profiles (The differences in percent deamidation are within assay variability.). There are no observable changes in the samples as seen by reducing SDS-PAGE/western blot and IEF/western blot. There is a slight decrease in the protein concentration. The decrease in protein concentration for the −70 degrees C. may due to the sample going through one freeze/thaw cycle. The decrease of protein concentration is still within 15% of the initial concentration.

Example 8

Preclinical Studies

A single intramuscular (IM) dose local tolerability study in rabbits is conducted which evaluates the local toxicity of interferon when administered in several new formulations. Injection site reactions due to administration of the present liquid formulation or with lyophilized and reconstituted interferon formulations are comparable to those evident following administration of normal saline.
1. Rabbit Irritation/Bioavailability Study Following Single Dose IM Administration of Four Formulations of Interferon-Beta)

Twenty male New Zealand white rabbits each received a single 30 ug intramuscular (IM) injection of Interferon beta-1a as one of five formulations: BG9589-1 (pH 5.0, acetate buffer, arginine stabilizer, 0.5 ml/dose); BG9589-2 (pH 5.0, acetate buffer, glycine/NaCl stabilizer, 0.5 ml/dose); BG9589-3 (pH 7.2, phosphate buffer, arginine stabilizer, 0.5 ml/dose); BG9589-4 (pH 7.2, phosphate buffer, glycine/NaCl stabilizer, 0.5 ml/dose); and a lyophilized interferon-beta formulation at pH 7.2 containing 1.5% HSA, 1.0 ml/dose (See Jacobs et al., supra).

Four animals received each treatment. Animals that received BG9589-1 or the lyophilized formulation also received an equivalent volume injection of normal saline in a contralateral site as a negative control. Blood samples are collected through 72 hours post-dose for serum interferon beta activity analyses. Macroscopic dermal evaluations for erythema, scar formation and edema are conducted at 6, 12, 24, 48 and 72 hours post-dose. Following the 72 hour post-dose blood collection, the animals are sacrificed, the injection sites are inspected macroscopically for signs of tissue damage and then fixed in 10% neutral buffered formalin. The muscle samples (three/injection site) are examined microscopically for inflammation, necrosis, hemorrhage and lesions.

Results:

When graded by Primary Irritation Index scores (EPA Dermal Classification System), none of the above liquid formulations were determined to be more than a slight skin irritant. Macroscopic inspection of a BG9589-4 injection site in one animal indicated slight irritation (hemorrhage); however microscopic investigation revealed no signs of hemorrhage and the macroscopic observation was determined to be an artifact. In short, microscopic examinations reveals that the liquid formulation test article injection site reactions were consistently minimal to mild and that no reaction was more severe than those induced by administration of the lyophilized formulation or normal saline.

In addition, rabbit dermal irritation following repeated IM administrations of the liquid formulations may easily be tested using multiple groups of rabbits that will receive intramuscular injections of liquid formulations or normal saline every other day for eight days (five doses total). Doses are administered in a pre-defined area on each animal's back to maximize local exposure to test article. Macroscopic dermal evaluations are conducted at 4-6 hours following each administration and 24 hours following the last administration for each treatment group. Daily gross observations are made at the time of each dermal evaluation. Following the 24 hour post-dose macroscopic examination, the animals are sacrificed, the injection sites will be inspected for signs of tissue damage and the tissue fixed in 10% neutral buffered formalin. The preserved tissues are examined microscopically for inflammation, necrosis, hemorrhage, and lesions. Blood samples also are collected immediately prior to the initial test article administration and at the time of sacrifice for hematology and serum chemistry evaluations.

Example 9

Clinical Studies

The present liquid formulations differ significantly from prior interferon formulations. For any clinical indication, there is the potential for a change in pharmacokinetic and pharmacodynamic behavior of the interferon when administered to humans. Unfortunately, the activities of interferon-beta are highly species specific and the most pertinent pharmacologic information is derived from studies in human cells in culture, in humans, and, to a lesser extent, in rhesus monkeys. A preferred way to test for pharmacological change, if any, is to conduct a human bioequivalence trial.

Anti-viral levels of interferon-beta in serum can be quantitated using a cytopathic effect (CPE) bioassay, as described for instance in Example 1. A human bioequivalence study can be conducted with any number of liquid and lyophilized interferon formulations. Through analysis of serum, area under the curve (AUC) and $C_{MAX}$ activity parameters, one of ordinary skill can determine whether lyophilized and liquid formulations are bioequivalent. As but one example of a bioequivalence study protocol, we describe briefly a double-blind, single-dose, crossover study to demonstrate the bioequivalence of a liquid formulation of the invention and a lyophilized interferon-beta product in healthy volunteers. Design. Each subject receives the same dosage (e.g., 60 ug 12 MU) of interferon-beta formulations in a double-blind, two-period crossover (Table 4). Subjects are between the ages of 18 and 45 years, inclusive and within 15% of the normal body weight range for height and body frame. Blood samples for hematology, chemistry, serum interferon beta activity and pharmacodynamic profiles are drawn immediately prior to, and at various times following, each dose, through 144 hours post-dose. Assessment of injection pain and injection site reactions also is followed.

Study Conduct.

As prophylaxis against interferon-associated flu-syndrome, all subjects will receive acetaminophen immediately before and throughout the dosing periods.

Pharmacokinetics.

Serum Interferon Beta Determinations.

Serum levels are measured as units of antiviral activity by a (CPE) assay. Serum antiviral levels are analyzed for AUC, $C_{max}$ and $T_{max}$. AUC values will be calculated from time of dosing to the last detectable level ($AUC_{0-T}$) and through 144 hours post dose ($AUC_{0-144}$). Standard descriptive analysis of the treatment data are conducted using SAS (version 6.08, SAS Institute, Cary, N.C.).

TABLE 5

Dose schedule for Exemplary Study

| Dose Group | Route | Dose (MU) | Treatment Period: 1 | Treatment Period: 2 |
|---|---|---|---|---|
| 1 | IM | 12 | Lyophilized (60 mcg) | Liquid (60 mcg) |
| 2 | IM | 12 | Liquid (60 mcg) | Lyophilized (60 mcg) |

Pharmacodynamics.

The biological marker neopterin, a product of the interferon induced enzyme GTP cyclohydrolase which reflects macrophage and T-cell activation (C. Huber et al., *J Exp Med* 1984; 160: 310-314; Sep. 20, 1996; D. Fuchs et al., *Immunol. Today* 9: 150-155, 1988) has been characterized. In both nonclinical and clinical studies of recombinant human interferon beta, induction of neopterin correlates with serum activity levels following administration of various recombinant human interferon beta treatments.

Neopterin is measured via standard laboratory procedures. The pharmacodynamic profile of interferon-beta is described in a quantitative manner by calculation of three serum neopterin parameters. The first parameter, $E_{AUC}$, is the area under the neopterin vs time curve normalized to baseline level. The second parameter is $E_{MAX}$; this parameter is the difference between the observed peak neopterin level and the baseline neopterin level. The third parameter is the induction ratio, IR; this parameter is calculated as the peak neopterin level divided by the baseline neopterin level.

Statistics.

The Wilcoxon-Mann-Whitney two, one-sided tests procedure is used on AUC to determine equivalence. To estimate the relative bioavailability of interferon from the liquid formulation relative to the lyophilized formulation and its 90% confidence limits, AUC is submitted to an analysis of variance (ANOVA) after logarithmic transformation. From the "between-subject" variation, the sequences and genders are isolated. From the "within-subjects" variation, components due to periods and treatments are isolated.

EQUIVALENTS

Other embodiments and uses of the invention will be apparent to those skilled in the art from consideration of the specification and practice of the invention disclosed therein. It is intended that the specification and examples be considered exemplary only, with the true scope and spirit of the invention being indicated by the following claims.

The invention claimed is:

1. A liquid formulation comprising: (i) an interferon-beta, and (ii) between about 0.3% and 5% by weight of an amino acid selected from the group consisting of acidic amino acids, arginine and glycine, wherein the formulation does not comprise serum albumin and; wherein the formulation has not been previously lyophilized.

2. The formulation of claim 1, wherein the formulation has a pH of between about 4.0 and 7.2.

3. The formulation of claim 1, wherein the formulation has a pH of between about 4.0 and 5.0.

4. The formulation of claim 1, wherein the formulation has a pH of between about 4.5 and 5.5.

5. The formulation of claim 1, wherein the formulation has a pH of between about 4.8 and 5.2.

6. The formulation of claim 1, wherein the arginine is arginine-HCl.

7. The formulation of claim 1, wherein the interferon-beta is present at between 6 MIU/ml and 50 MIU/ml.

8. The formulation of claim 1, wherein the formulation further comprises a solution of a weak acid comprising acetate and acetate salt.

9. The formulation of claim 8, wherein the acetate or acetate salt is present at 20 mM.

10. The formulation of claim 1, further comprising a surfactant.

11. The formulation of claim 10, wherein the surfactant is 0.1% (w/v) PLURONIC F-68.

12. The formulation of claim 1, wherein said liquid formulation has a dissolved oxygen level that is less than 30% of atmospheric equilibrium levels.

13. The formulation of claim 12, wherein said liquid formulation has a dissolved oxygen level that is less than or equal to 10% of atmospheric equilibrium levels.

14. A liquid formulation comprising: (i) an interferon-beta present at between 6 MIU/ml and 50 MIU/ml and (ii) between about 0.3% and 5% by weight of arginine-HCl, wherein the formulation does not comprise serum albumin, wherein the formulation has not been previously lyophilized, wherein the formulation has a pH of between 4.8 and 5.2, wherein the formulation further comprises an acetate or acetate salt present at 20 mM and; wherein the formulation further comprises a surfactant, and; wherein the formulation has a dissolved oxygen level that is less than or equal to 10% of atmospheric equilibrium levels.

15. A packaged kit for parenteral administration of an interferon-beta, the kit containing a syringe pre-filled with a liquid formulation comprising the interferon-beta and an acidic amino acid stabilizing agent selected from the group consisting of acidic amino acids, arginine and glycine; wherein the amino acid stabilizing agent is present at between 0.3% and 5% w/v; wherein the liquid formulation has not been reconstituted from lyophilized interferon; wherein the liquid formulation is not further lyophilized, wherein the liquid formulation does not comprise serum albumin, and wherein the syringe has a head space flushed with an inert gas.

16. The packaged kit of claim 15, wherein at least one surface of the syringe in contact with the liquid formulation is coated with a material inert to interferon.

17. The packaged kit of claim 15, wherein the formulation has not been cavitated.

18. The packaged kit of claim 15, wherein the formulation has a pH of between about 4.0 and 7.2.

19. The packaged kit of claim 15, wherein the formulation has a pH of between about 4.0 and 5.0.

20. The packaged kit of claim 15, wherein the formulation has a pH of between about 4.5 and 5.5.

21. The packaged kit of claim 15, wherein the formulation has a pH of between about 4.8 and 5.2.

22. The packaged kit of claim 15, wherein the arginine is arginine-HCl.

23. The packaged kit of claim 15, wherein the interferon-beta is present at between 6 MIU/ml and 50 MIU/ml.

24. The packaged kit of claim 15, wherein the formulation further comprises a solution of a weak acid comprising acetate and acetate salt.

25. The packaged kit of claim 24, wherein the acetate or acetate salt is present at 20 mM.

26. The packaged kit of claim 15, wherein the formulation further comprises a surfactant.

27. The packaged kit of claim 26, wherein the surfactant is 0.1% (w/v) PLURONIC F-68.

28. The packaged kit of claim 15, wherein said liquid formulation has a dissolved oxygen level that is less than 30% of atmospheric equilibrium levels.

29. The packaged kit of claim 28, wherein said liquid formulation has a dissolved oxygen level that is less than or equal to 10% of atmospheric equilibrium levels.

* * * * *